(12) United States Patent
Aleid et al.

(10) Patent No.: US 8,323,717 B2
(45) Date of Patent: Dec. 4, 2012

(54) METHOD OF PRODUCING BAKER'S YEAST

(75) Inventors: Salah Mohammed Aleid, Alhassa (SA); Siddig Hussein Hamad, Alhassa (SA); Fahad Mohammed Al-Jasass, Riyadh (SA)

(73) Assignees: King Faisal University, Alahsa (SA); King Abdulaziz City for Science and Technology, Riyadh (SA)

( * ) Notice: Subject to any disclaimer, the term of this patent is extended or adjusted under 35 U.S.C. 154(b) by 0 days.

(21) Appl. No.: 12/954,534

(22) Filed: Nov. 24, 2010

(65) Prior Publication Data

US 2012/0128853 A1  May 24, 2012

(51) Int. Cl.
*C12N 1/00* (2006.01)
*A21D 13/00* (2006.01)
*A23L 1/28* (2006.01)

(52) U.S. Cl. .................. 426/549; 435/254.2; 435/255.1; 435/255.2; 435/255.21; 426/60

(58) Field of Classification Search .................. None
See application file for complete search history.

(56) References Cited

OTHER PUBLICATIONS

Al-Jasass, Fahad M; Al-Eid, Salah, M; and Ali, Siddig H.H. ; A comparative study on date syrup (dips) as substrate for the production of baker's yeast (*Saccharomyces cerevisiae*) JFAE 8(2):314-316, Apr. 2010 (abstract).*
Acourene, S, Khalid, A. Kh., Bacha, A, Tama, M, Taleb, B. Optimization of Bakery Yeast Production Cultivated on Musts of Dates. Journal of Applied Sciences Research 3(10):964-971, 2007.*
Beiroti, A and Hosseini, SN. Production of baker's yeast using date juice. Sheng Wu Gong Chen Xue Bao ( Chinese Journal of Biotechnology) 23(4):746-750, Jul. 2007 (abstract).*
Gomez, Pastor, R; Perez-Torrado, R; Garre, E; Matallana, E. "Recent Advances in Yeast Biomass Production", in "Biomass: Detection, Production, and Usage" Book Chapter, ISBN 978-953-307-492-4; Sep. 2011. http://www.intechopen.com/source/pdfs/19075/InTech-Recent_advances_in_yeast_biomass_production.pdf :, accessed on Nov. 14, 2011.*
Acourene, S and Ammouche, A. Optimization of Culture Medium of Baker's Yeast, Ethanol, Citric Acid and Alpha-Amylase Production from Dates Syrup. Research Journal of Agriculture and Biological Sciences, 6(6):846-860, 2010.*
"Utilization of Saudi date sugars in production of baker's yeast", Khan et al., Bioresource Technology, vol. 53, Issue 1 (1995), pp. 63-66 (Abstract only).

(Continued)

*Primary Examiner* — Humera Sheikh
*Assistant Examiner* — Subbalakshmi Prakash
(74) *Attorney, Agent, or Firm* — Richard C. Litman (57) ABSTRACT

The method of producing baker's yeast involves producing yeast from a substrate composed of date syrup (Dips) diluted by molasses in sufficient quantity to lower the concentration of organic acids present in the date syrup that are toxic to yeast to safe levels, preferably a 1:1 mixture (w/w) of date syrup (Dips) and molasses. The substrate is inoculated with viable cells of *Saccharomyces cerevisiae* yeast and placed in a bioreactor or fermentation vessel. The yeast is produced by a fed-batch process to ensure continuous yeast production and prevent or minimize the production of alcohol by the yeast, additional increments of the substrate being added about hourly for the duration (about 12 hours) of the yeast propagation process. The process produces baker's yeast comparable in quality to yeast produced from a pure molasses substrate for such purposes as making bread, and in sufficient quantity to be practical for industrial production.

13 Claims, 3 Drawing Sheets

Propagation of *S. cerevisiae* NCYC 1530 on Molasses Substrate

OTHER PUBLICATIONS

"Date Syrup and Baker's Yeast Production", Alemzadeh et al., Ind. Eng. Chem. Res., 41, 128-130 (2002).

"Optimization of Bakery Yeast Production Cultivated on Musts of Dates", Acourene et al., Journal of Applied Sciences Research, 3(10): 964-971 (2007).

"Production of baker's yeast using date juice", Beirote A. Hosseini, Sheng Wu Gong Cheng Xue Bao, 23(4): 746-750 (Jul. 2007) (Abstract only).

"Peerformance of baker's yeast produced using date syrup substrate on Arabic bread quality", A-Eid et al., African Journal of Biotechnology, vol. 9(21), 3167-3174 (May 2010).

* cited by examiner

Propagation of *S. cerevisiae* NCYC 1530 on Molasses Substrate

Fig. 1

Propagation of *S. cerevisiae* NCYC 1530 on Dips Substrate

Fig. 2

**Propagation of *S. cerevisiae* NCYC 1530 on 2:1 Dips/Molasses Substrate**

*Fig. 3*

**Propagation of *S. cerevisiae* NCYC 1530 on 1:1 Dips/Molasses Substrate**

METHOD OF PRODUCING BAKER'S YEAST

BACKGROUND OF THE INVENTION

1. Field of the Invention

The present invention relates to fermentation processes and processes for the production of yeast, and particularly to a method of producing baker's yeast that uses date syrup as part of the substrate.

2. Description of the Related Art

The economic utilization of dates is a very important issue to the Kingdom of Saudi Arabia because this crop is the most important agricultural produce of the country. The date crop is also the historical staple in the whole area, having a very high religious and cultural significance, which makes the continuation of its production at the highest possible levels a national priority. Thus, Saudi Arabia is one of the major date producers in the world, with an annual production of about one million tons of date fruits. About 50% of this amount is consumed locally as human food, 4% exported and 4% used as animal feed. More than 40% of the annual produce, i.e., about 400 thousand tons, mainly fruits of the low quality Rezez variety, represents a surplus for which there is currently no economic use. Rezez is produced in large quantities because the tree can grow in marginal soils without much need for fertilization, but still gives high yields of fruits.

Baker's yeast is a type of yeast used in the production of leavened bread, cakes, pastries, and other bakery products. Baker's yeast converts the fermentable sugars in dough into carbon dioxide and ethanol. The most common strain of yeast in baker's yeast is *Saccharomyces cerevisiae*, which is also used in fermentation processes for the production of alcoholic beverages. Baker's yeast may be processed so that it is available to the user in a variety of forms, including dry yeast (which may be in cakes or in granules) and liquid yeast, and in active or dehydrated forms.

Baker's yeast can be produced from substrates that contain metabolizable sources of carbon, energy, nitrogen, minerals and essential vitamins. Substrates that contain carbon and energy sources readily metabolizable for *Saccharomyces cerevisiae* can be directly used for production of baker's yeast, while those containing complex carbohydrates, such as starches in grains and cellulose in green or woody plants, need costly hydrolytic treatment before use. The substrate of choice for baker's yeast production in the world today is molasses derived from beets or sugar cane.

Saudi Arabia imports all of its local market needs for baker's yeast, which amounts to about 10 thousand tons per year. A factory for the production of baker's yeast that was based in the city of Jeddah, in the west of the country, stopped production, partly due to the high cost of imported molasses substrate. Thus, the high cost of the raw materials for the production of baker's yeast has caused Saudi Arabia and many other Gulf Coast countries to rely upon importation of baker's yeast to meet demand.

Commercial baker's yeasts produced from strains of *Saccharomyces cerevisiae* have the following average chemical composition: 47% C, 32% $O_2$, 6% $H_2$, 7.7% $N_2$, 2% K, 1.2% P, 1% S, 0.2% Mg, 0.1% Na, and other trace elements. In addition, the yeast cells contain small amounts of vitamin B complex, of which D-Pantothenic acid, D-Biotin and m-Inositol are essential because the yeast cells cannot synthesize them. These elements and compounds must be provided in the production medium in enough quantities and metabolizable forms.

Dates are known to contain a variety of simple sugars, and may contain 65-87% sugars, 1-3% proteins, in addition to many minerals important for yeast nutrition, including potassium, magnesium, sulphur, phosphorus, iron, calcium, and chlorine. Although various laboratory studies have suggested that it may be theoretically possible to use portions of or extracts from dates as a substrate for the production of baker's yeast, it has not been practical to do so industrially because it has not been shown that the process is economically efficient, i.e., the biomass of yeast produced from a given mass of substrate has not been high enough or efficient enough to justify the expenditure in raw materials for the substrate and nutrients, the labor, the capital equipment, and other costs for production, transport, and delivery to the consumer. It has been reported that the optimum biomass concentration in the fermentation medium for economical production is about 40 g/l, which existing methods and processes have not come close to.

Thus, a method of producing baker's yeast solving the aforementioned problems is desired.

SUMMARY OF THE INVENTION

The method of producing baker's yeast involves producing yeast from a substrate composed of date syrup diluted by molasses in sufficient quantity to lower the concentration of organic acids present in the date syrup that are toxic to yeast to safe levels, preferably a 1:1 mixture (w/w) of date syrup (Dips) and molasses. The substrate is inoculated with viable cells of *Saccharomyces cerevisiae* yeast and placed in a bioreactor or fermentation vessel. The yeast is produced by a fed-batch process to ensure continuous yeast production and prevent or minimize the production of alcohol by the yeast, additional increments of the substrate being added about hourly for the duration (about 12 hours) of the yeast propagation process. The process produces baker's yeast comparable in quality to yeast produced from a pure molasses substrate for such purposes as making bread, and in sufficient quantity to be practical for industrial production of baker's yeast.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The method of producing baker's yeast involves producing yeast from a substrate composed of date syrup (Dips) diluted by molasses in sufficient quantity to lower the concentration of organic acids present in the date syrup that are toxic to yeast to safe levels, preferably a 1:1 mixture (w/w) of date syrup (Dips) and molasses. The substrate is inoculated with viable cells of Saccharomyces cerevisiae yeast and placed in a bioreactor or fermentation vessel. The yeast is produced by a fed-batch process to ensure continuous yeast production and prevent or minimize the production of alcohol by the yeast, additional increments of the substrate being added about hourly for the duration (about 12 hours) of the yeast propagation process. The process produces baker's yeast comparable in quality to yeast produced from a pure molasses substrate for such purposes as making bread, and in sufficient quantity to be practical for industrial production of baker's yeast.

Date syrup was chemically analyzed to determine its contents for comparison to nutrients needed by baker's yeast (Saccharomyces cerevisiae), and also to determine the presence of chemicals that could be toxic to the yeast. The results presented in Table 1 show that date syrup contained about 80% total sugars, i.e., 800 kg/ton, mainly in the form of fructose (41%), and glucose (38%), and a small amount of sucrose (1%). It also contained 2% crude protein, 1.13 g/kg phosphorus, 14.88 g/kg potassium, 0.79 g/kg magnesium, 240 ppm pantothenic acid, 2.73 ppm biotin, and no detectable amounts of m-Inositol.

These results indicate that date syrup can be used as a main source of carbon and energy for baker's yeast production. Calculations based on the chemical composition of date syrup shown in Table 1 give the following. Since a ton of date syrup contains 800 kg sugar, then this ton, regarded as a carbon and energy source, should produce about 400 kg dry yeast, because one kg sugar is known to yield about 0.5 kg yeast dry matter, i.e., we need about 2.5 kg of date syrup for every kilogram of yeast dry matter produced. The protein content of date syrup is about 2%, i.e., 20 g/kg, whereas baker's yeast contains about 50% proteins, i.e., 500 g/kg yeast dry matter. This means that one kg yeast (i.e., 500 g protein) contains about 80 g nitrogen (16% nitrogen in protein), and the nitrogen content in 2.5 kg date syrup available to produce one kg yeast (see above) is about 8 g of nitrogen. Hence, there is a deficiency of about 72 g nitrogen for every kg yeast produced. This nitrogen deficiency in date syrup must be covered by adding to the production medium inorganic nitrogen sources, such as ammonium salts. The phosphorus content in date syrup is 1.13 g/kg (about 2.8 g/2.5 kg date syrup), compared to 14.1 g/kg in the yeast; i.e., date syrup is deficient in phosphorus, which has to be added to the production substrate in the form of inorganic phosphorus at about 11.5 g phosphorus for every kg of yeast produced. The magnesium content in date syrup is 0.79 g/kg (about 2 g/2.5 kg Date syrup), and its content in baker's yeast is 2 g/kg, so that the magnesium content in date syrup is just enough. No m-Inositol was detected in date syrup. Thus, about 2 g of this compound must be added to the production medium for every kg of yeast produced. The potassium content of date syrup is about 15 g/kg (37 g/2.5 kg Date syrup), whereas the content of potassium in yeast is about 20 g/kg yeast dry matter. This means that the potassium content in date syrup is enough for baker's yeast production. Similar calculations show that biotin and pantothenic acid are present in date syrup in quantities sufficient for baker's yeast production.

TABLE 1

Nutrients in date syrup compared to requirements of baker's yeast

| Chemicals | Concentration in date syrup | Content in Baker's yeast |
| --- | --- | --- |
| Phosphorus (g/kg) | 1.13 | 14.10 |
| Potassium (g/kg) | 14.88 | 20 |
| Magnesium (g/kg) | 0.79 | 2 |
| Total sugars (%) | 80 | 30 |
| Fructose | 41 | |
| Glucose | 38 | |
| Sucrose | 1 | |
| Crude protein (%) | 2 | 50 |
| Pantothenic acid (ppm) | 240 | 150 |
| Biotin (ppm) | 2.73 | 0.30 |
| m-Inositol (ppm) | 0 | 2000 |

To compensate for the deficiencies in nutrients mentioned above, mineral media with compositions as shown in Table 2 were used in our laboratories to try to obtain production of up to 40 g/l yeast dry matter (e.g. 400 g yeast in a 10 liter fermentation volume). The substrates used were pure date syrup and, separately, molasses alone. The molasses substrate gave satisfactory yield, while the yield from pure date syrup was unsatisfactory. The reduced yield from pure date syrup substrate was attributed to the presence of compounds toxic to the yeast in date syrup.

TABLE 2

Composition of mineral media required for 400 g yeast dry matter

| | Amount (g) | |
| --- | --- | --- |
| Chemicals | 100% molasses | 100% date syrup |
| $(NH_4)_2SO_4$ | 61 | 60 |
| $(NH_4)_2HPO_4$ | 54 | 53 |
| Pantothenic acid | 0.025 | 0 |
| m-Inositol | 0 | 0.8 |

With regard to its content of nutrients, date syrup can compare very well with molasses, which is the conventional substrate for baker's yeast production world wide, as shown in Table 3. Date syrup contains much more sugar, biotin and pantothenic acid than molasses, about similar content of nitrogen, phosphorus and magnesium, about half the content of potassium (but still enough for baker's yeast production), but much less m-Inositol.

TABLE 3

Nutrient composition of date syrup compared to molasses

| Nutrient | Date syrup | Beet molasses | Cane molasses |
| --- | --- | --- | --- |
| Sugars (%) | 80 | 50 | 50 |
| Nitrogen (%) | 0.13 | 0.5 | 0.1 |
| Phosphorus (%) | 0.11 | 0.03 | 0.09 |
| Potassium (%) | 1.5 | 3.0 | 3.0 |
| Magnesium (%) | 0.08 | 0.01 | 0.3 |
| Biotin (ppm) | 2.73 | 0.05 | 2.0 |
| Pantothenic acid (ppm) | 240 | 80 | 25 |
| m-Inositol (ppm) | 0 | 6500 | 2000 |

Compounds toxic to baker's yeast detected in date syrup include formic acid at 3.06%, acetic acid at 2.38%, and propionic acid at 0.68%, (total acids 6.12%), and no detectable amounts of the toxicants nitrite, sulfite and butyric acid (see Table 4). Formic acid becomes toxic to the yeast when its concentration in the medium exceeds 0.25% (w/v), whereas the toxicity level of the other two acids is in excess of 3.0% (w/v) for the sum of the two. In baker's yeast fermentation, a maximum of about 40 g/l yeast dry matter end concentration in the fermentor can be reached. In industrial fermentations this will mean adding date syrup to the mineral medium to an end dilution of 1:10 (Date syrup:medium). Since date syrup is added in a fed-batch process, the concentration of toxic acids will increase gradually to reach about 0.3% for formic acid and about 0.7% for total acids at the end of fermentation (the amount present in date syrup diluted 1:10). This end concentration of formic acid is within levels toxic to baker's yeast. Fermentation experiments done in our laboratories confirmed this, where only 50-60% of the theoretical yields were obtained when pure date syrup was used as substrate.

In the examples below, the following materials, equipment, and procedures were used.

Glucose, Fructose, Sucrose and m-Inositol concentrations were determined with High Performance Liquid Chromatography (HPLC) using a Shimadzu Japan Model 2003, equipped with a RID 10A refractive index detector, CLC $NH_2$ 6×150 column, LC 10ATP pump, and CTO 10AC VP oven. Mobile phase was 83% $CH_3CN$:17% water (v/v), flow rate 1 ml/min., column pressure 200 $KgF/cm^2$. Ethanol was determined enzymatically using the UV-method (Boehringer, Mannheim/R-Biopharm). Biotin and pantothenic acid were determined according to the vitaFast (r-biopharm) vitamin testing method, using ELISA Reader, Multiskan EX Model No. 355, Thermolabsystem-Finlan. Phosphorus, potassium, magnesium, sulfur, and crude protein, were determined according to A.O.A.C. standard methods of analysis (1992). Formic, acetic, propionic and butyric acids were determined using Gas Liquid Chromatography, Column: LiChroCART 125-4, Purospher RP-18 e, 5 µm; mobile phase: A: 20 mM sodium dihydrogen phosphate, pH 2.5; B: Acetonitrile; Detection: UV 220 nm). Yeast biomass was determined using the dry matter method after centrifugation of 5 ml broth at 2000 rpm for 5 minutes in a dry centrifugal tube, and overnight drying at 105° C.

Date syrup (Dips, an Arabic name) used in the fermentation experiments was obtained from a factory operating in Hofuf City, Saudi Arabia. Its extraction process was as follows: de-pitted fruits (Rezez variety) were heated with equal amount of water at 80° C. for 30 minutes, and then filtered using a filter press and a micro filter (Filtrox AG, CH 9000 St. Gallen, Switzerland), and finally concentrated to 80 Brix at 80° C. under vacuum to give the syrup named Dips. Sugar cane molasses was obtained from the local market. It was a product imported from Egypt.

The yeast strain used in this study was a *Saccharomyces cerevisiae* NCYC 1530 brought from the laboratories of the National Center for Yeast Collection, Institute of Food Research, Norwich, Great Britain.

Inoculum size used in all fermentations was 8 g/l. The yeast was first propagated in the bioreactor in fed-batch processes, then filtered to yeast cake, and then kept in the refrigerator for use as inoculum.

Four substrates were used for propagation, namely, 100% Rezez Dips as the substrate of study, 2:1 and 1:1 Dips/molasses (weight/weight) as a trial to remove deficiencies in Dips alone, and 100% cane molasses as a reference substrate. The substrates were prepared as follows: dilution with water to give sugar concentrations of about 20%, pH brought to 4.5 with $H_2SO_4$, and then heating to boiling for about 20 minutes. This treatment clarifies the substrate from suspended matter, which is left to precipitate, and the clear supernatant decanted and then sterilized in 5-liter bottles by autoclaving at 121° C. for 30 minutes.

The mineral medium was formulated after chemical analysis of Rezez Dips and molasses substrates used for propagation and comparison of their nutrient content with the needs of baker's yeasts (Bronn, 1990). For each fermentation run (to produce a maximum of 220 g yeast from 440 g sugar fed to the fermentor), 45 g $(NH_4)_2HPO_4$ and 45 g $(NH_4)_2SO_4$ were used as mineral medium, in addition to 15 mg Pantothenic acid for the molasses substrate, and 10 g $MgSO_4$ and 0.5 g m-Inositol for the Dips substrate (magnesium content of Dips was marginal). No vitamins or magnesium sulfate were added to the mixed substrate. The nutrients were dissolved in 6 liters distilled water in the bioreactor, the pH adjusted to 4.5, and then autoclaved for 30 minutes at 121° C.

Fermentations were carried out in a BioFlo 110 bioreactor (New Brunswick Scientific, New Jersey, USA) with 10-liter working volume. All runs were fed-batch processes, at 30° C., 8 g/l inoculum size, 6.0 liter starting volume, and sugar concentration in all substrates was 200 g/l. Totals of 440 g sugar (2.2 liter substrate) were pumped into the bioreactor, the feeding starting at 12 g/h sugar, then increased every hour to reach a maximum of 53 g/h in 9 hours, then kept constant till the end of propagation (8.2 liter end volume in the bioreactor). This feeding strategy was supposed to give a maximum of about 35 g/l yeast concentration in the bioreactor, and the growth rate of the yeast should not exceed a critical value of about $0.2\ h^{-1}$ to avoid respirofermentative growth and formation of ethanol due to the Crabtree Effect common to all *Saccharomyces cerevisiae* strains (the critical growth rate was calculated according to (Bronn, (1990)). Fermentation time was 12 hours and samples were taken every hour for analysis.

The viable cell counts of the yeast were determined by plating on Potato Dextrose Agar (PDA, Oxoid CM0139) and incubation for 2-4 days at 30° C. The theoretical yield of yeast biomass on sugar ($Y_{x/s}$) is 0.5 g yeast dry matter per g sugar (Bailey and Ollis, 1986). The actual yields were calculated by dividing yeast biomass produced by the amount of sugar fed to the fermentor.

Example 1

To try to remove the toxic compounds (the volatile organic acids) from Date syrup, and hence increase yield, the following treatment was applied. A treatment similar to one performed for molasses clarification in baker's yeast factories (for the removal of similar compounds) was performed as follows. Date syrup was diluted 1:3 with water, pH brought to 4.5 with sulfuric acid, and then it was boiled in an open container under continuous aeration for about 15 minutes. This treatment did not bring about the desirable effect, as can be seen from Table 4. This can be due to the fact that our treatment was performed in a simple pot, while the treatment of molasses is typically done in equipment specially designed for this purpose, with heating up to 140° C. under pressure followed by release of pressure and injection of air, which can result in a more effective evaporation of the volatile toxic compounds. Such equipment is not available to us now, but can be regarded as a possible solution in plants for commercial production.

TABLE 4

Contents of chemicals toxic to baker's yeast in date syrup

| Chemical | Toxicity level (%) in yeast substrate* | | Concentration (%) in Date syrup | |
|---|---|---|---|---|
| | Tolerable | Toxic | Untreated | Treated |
| Nitrite | <0.001 | Up to 0.05 | 0 | 0 |
| Sulfite | <0.01 | >0.15 | 0 | 0 |
| Formic acid | <0.1 | >0.25 | 3.06 | 2.81 |
| Acetic acid | <1.0 | Up to 3.0 | 2.38 | 2.38 |
| Propionic acid | <1.0 | Up to 3.0 | 0.68 | 0.51 |
| Butyric acid | <1.0 | Up to 3.0 | 0 | 0 |

In Table 4, the data in columns two and three relating to the Toxicity Levels in the yeast substrate, both tolerable and toxic, are taken from Bronn, W., "Technology of Baker's Yeast Production" (in German), Technical University of Berlin, Germany (1990).

Example 2

Since conventional treatment did not eliminate the toxins intrinsic to date syrup, the present inventors decided to try diluting the toxins in date syrup to a tolerable level by adding molasses to the date syrup substrate. Therefore, a comparative experiment was designed using four substrates: pure molasses, pure date syrup, a 1:1 date syrup/molasses dilution, and a 2:1 date syrup/molasses dilution.

Chemical analysis of Rezez Date syrup and cane molasses used in this study showed that the two substrates contained comparable amounts of nutrients needed by baker's yeast, as shown in Table 5. Both are good sources of carbon and energy, and contain enough amounts of potassium, magnesium and the essential vitamin biotin. The deficient nutrients are nitrogen and phosphorus in both substrates, sulfur and the essential vitamin m-Inositol in date syrup, and the essential vitamin pantothenic acid in molasses.

TABLE 5

Nutrients required to produce 1 kg yeast dry matter

| Nutrient | Content in 2.5 kg of Rezez Date syrup | Content in 3.4 kg of cane molasses | Content in 1 kg of baker's yeast* | Deficiency in Date syrup | Deficiency in molasses |
|---|---|---|---|---|---|
| Phosphorus (g) | 2.8 | 3.0 | 13 | 10.2 | 10 |
| Potassium (g) | 37.3 | 102 | 20 | — | — |
| Magnesium (g) | 2 | 10.2 | 2 | — | — |
| Sulphur (g) | 1.2 | 17 | 10.8 | 9.6 | — |
| Nitrogen (g) | 3.2 | 3.4 | 80 | 76.8 | 76.6 |
| Pantothenic acid (mg) | 600 | 91.8 | 150 | — | 58.2 |
| Biotin (mg) | 6.8 | 7 | 0.3 | — | — |
| m-Inositol (g) | 0 | 13.6 | 2 | 2 | — |

Table 5 represents the contents of various nutrients (as shown by the inventors' chemical analysis) in 2.5 kg of Rezez date syrup and in 3.4 kg of molasses, the contents of the same nutrients in Baker's yeast as provided in the above reference by Bronn, and the calculated deficiency in the date syrup and in the molasses (based upon sugar content, it is estimated that 2.5 kg of the date syrup or 3.4 kg of the molasses are required to produce 1 kg of yeast (S. cerevisiae) dry matter).

Figure 1:
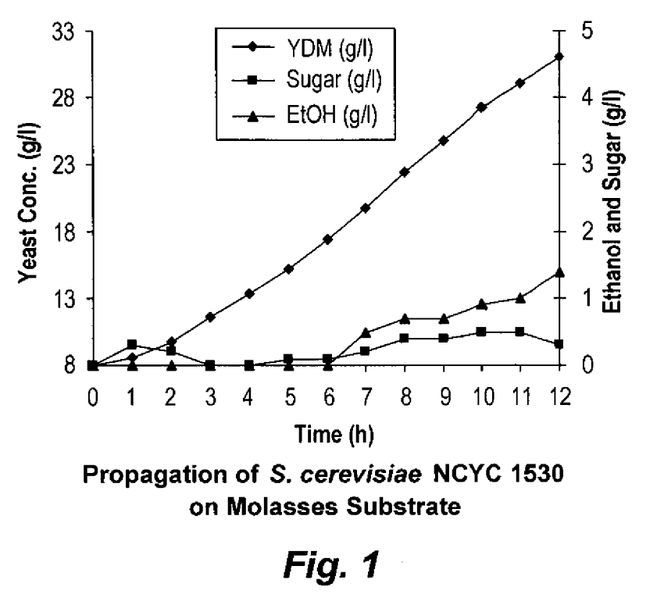
FIG. 1 is a graph showing the relative concentrations of yeast (YDM), sugar, and ethanol (EtOH) as a function of time when the yeast is propagated on a substrate of molasses.
Figure 2:
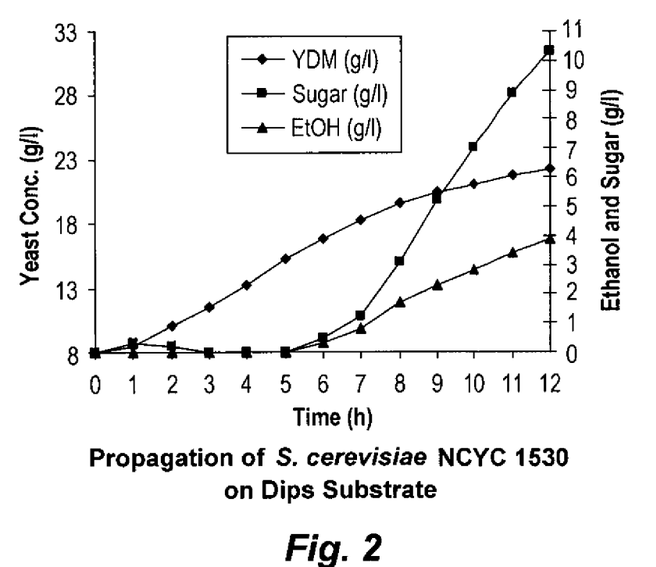
FIG. 2 is a graph showing the relative concentrations of yeast (YDM), sugar, and ethanol (EtOH) as a function of time when the yeast is propagated on a substrate of date syrup (Dips).

Propagation of the yeast on pure date syrup substrate gave much lower overall biomass yields compared to pure molasses substrate (FIGS. 1 and 2). In the first 5 hours of propagation, the yields from the two substrates were similar (Table 6).

The overall yields reached in this period were about 0.49 g yeast dry matter per gram of sugar for both substrates, representing 98% of the theoretical yield (total biomass produced was about 51 g yeast dry matter (FIGS. 1 and 2) from 104 g sugar fed). Only traces of sugar and ethanol were detected in the fermentation broth during propagation, indicating that the growth was fully oxidative and no respirofermentative metabolism was taking place. Starting from the sixth hour of propagation, the biomass yields of the yeast grown on date syrup substrate started to decrease, and reached 0.05 g/g in the last hour of propagation, when the growth was respirofermentative, i.e., ethanol was produced. At the end of propagation the maximum yeast biomass concentration reached was 22.2 g/l, 3.9 g/l ethanol was produced, and 10.3 g/l sugar remained unconsumed in the fermentation broth (FIG. 2 and Table 6). The average (from three runs) overall biomass yield on sugar was about 0.3 g yeast dry matter per gram of sugar, representing about 60% of the theory (Table 8).

TABLE 6

Biomass yields of S. cerevisiae NCYC 1530

| Time (h) | Molasses | Date syrup | Date syrup/molasses (2:1) | Date syrup/molasses (1:1) |
|---|---|---|---|---|
| 0 | 0 | 0 | 0 | 0 |
| 1 | 0.34 | 0.29 | 0.29 | 0.24 |
| 2 | 0.41 | 0.47 | 0.33 | 0.45 |
| 3 | 0.48 | 0.45 | 0.46 | 0.48 |
| 4 | 0.49 | 0.47 | 0.47 | 0.49 |
| 5 | 0.47 | 0.47 | 0.47 | 0.47 |
| 6 | 0.48 | 0.45 | 0.46 | 0.48 |
| 7 | 0.47 | 0.30 | 0.41 | 0.44 |
| 8 | 0.46 | 0.17 | 0.36 | 0.42 |
| 9 | 0.41 | 0.12 | 0.30 | 0.42 |
| 10 | 0.40 | 0.07 | 0.23 | 0.42 |
| 11 | 0.34 | 0.07 | 0.18 | 0.36 |
| 12 | 0.31 | 0.05 | 0.15 | 0.26 |

With respect to molasses, the biomass yield remained fairly constant till the eighth hour of propagation, the yeast growing oxidative, and no significant amounts of ethanol were formed or sugar accumulated in the fermentation broth. Starting from the ninth hour, the yields started to decrease and reached 0.31 g/g in the last hour of propagation, and 1.4 g/l ethanol was formed, but still no significant amounts of sugar remained in the broth (FIG. 1 and Table 6). The maximum biomass concentration reached at the end of propagation was 31 g/l, and the average (from three runs) overall yield on sugar from molasses substrate was about 0.47 g/g, representing about 94% of the theoretical yield. The yield from molasses substrate was significantly higher than that from date syrup substrate (Table 8). The decrease in yield from molasses substrate at the end of propagation can be explained by the fact that the biomass concentration reached a critical limit where oxygen supply was not enough to support fully oxidative growth. This was apparent in a drop of the dissolved oxygen concentration in the broth to about zero saturation, even when the stirring rate was raised to about 9000 rpm. According to Bailey and Ollis, "Biochemical engineering fundamentals", second edition. McGraw-Hill Book Company, New York (1986), p. 294, the critical oxygen concentration for oxidative growth of most microorganisms lies in the range 0.1 to 10% of the saturation solubility value of oxygen in water. As a result of a shortage in oxygen supply, the yeast cells seemed to have shifted to respirofermentative metabolism and produced ethanol at the expense of biomass.

With regard to the yeast grown on date syrup substrate, the conditions were different. No oxygen shortage was observed, since the dissolved oxygen concentration in the broth remained fairly above 10% saturation. The decrease in biomass yield can only be explained by the presence of yeast toxic organic acids, especially formic acid, at high concentrations in Rezez date syrup. The concentration of these acids in the 1:4 diluted date syrup substrate was about 0.75% formic and 0.50% acetic+propionic+butyric acids. No information was found in the literature about the organic acid content of date fruits. The Rezez date syrup used in this work was slightly acidic, with pH about 5. The organic acids of the fruit were concentrated in the date syrup during extraction (4-5 times), and they may have been natural products of the date fruit, or they may have been produced by bacterial contaminants. The concentration of these acids in the fermentation broth increased gradually with time as the substrate feeding to the fermentor proceeded, and reached toxic levels of 0.3 to 0.34% at the end of propagation (Table 7). This explains why the biomass yields were high at the beginning of propagation, where formic acid concentration was low, and then started to drop after a critical concentration of this acid was reached. According to the above-cited Bronn reference, baker's yeasts can tolerate up to 0.1% formic acid and up to 3.0% acetic+propionic+butyric acids, but these acids become toxic at concentrations above 0.25% for formic and above 3% for the other acids. No significant differences in viable cell counts were found between yeasts produced on date syrup and molasses substrates (Table 8), but the ones produced on date syrup had a much longer lag phase. Well-developed colonies developed in about 2 days of incubation in the case of yeasts from molasses, whereas those from date syrup needed 3 to 4 days to form comparable colonies. This indicates that these organic acids were more fungistatic rather than fungicidal.

TABLE 7

Concentration of organic acids toxic to Saccharomyces cerevisiae

| Substrate | Concentration (%) in broth at end of propagation | |
|---|---|---|
| | Formic acid | Acetic + propionic + butyric acids |
| Pure Date syrup | 0.3-0.34 | 0.36-0.41 |
| 2:1 Date syrup/molasses | 0.17-0.21 | 0.23-0.25 |
| 1:1 Date syrup/molasses | 0.11-0.14 | 0.16-0.20 |

TABLE 8

Comparison of yields and viable cell counts of S. cerevisiae NCYC 1530

| Substrate | Average yields (% of theoretical) | Viable cell counts ($\log_{10}$ cfu/g) |
|---|---|---|
| Molasses | 93.5[a] | 10.38[A] |
| Date syrup | 59.7[c] | 10.23[A] |
| 2:1 Date syrup/molasses | 80.4[b] | 10.30[A] |
| 1:1 Date syrup/molasses | 93.1[a] | 10.34[A] |

[a-c]Mean values within the same column bearing different superscripts are significantly different ($P \geq 0.05$)

Figure 3:
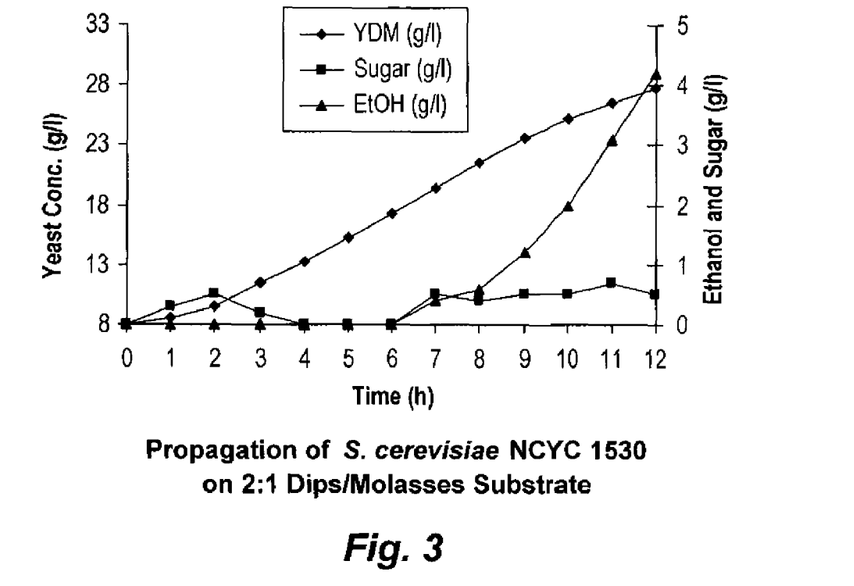
FIG. 3 is a graph showing the relative concentrations of yeast (YDM), sugar, and ethanol (EtOH) as a function of time when the yeast is propagated on a substrate of 2:1 date syrup (Dips)/molasses.
Figure 4:
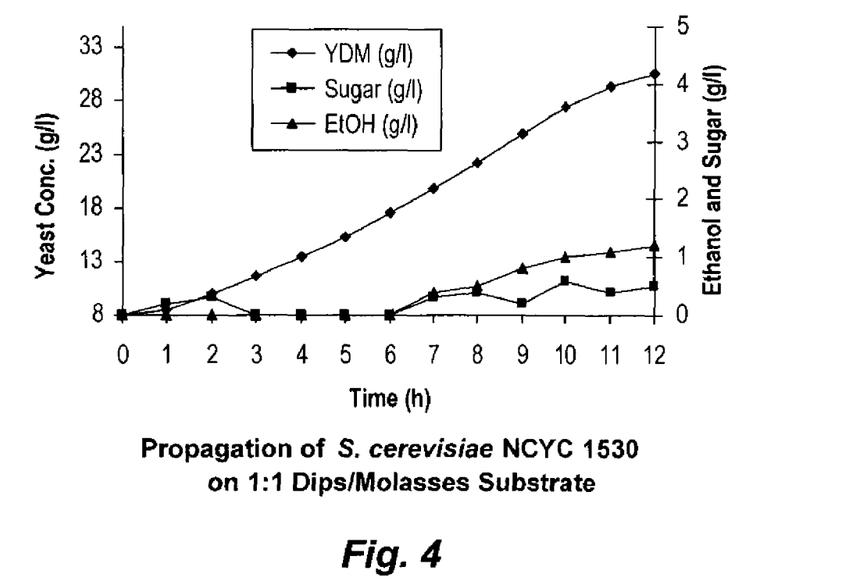
FIG. 4 is a graph showing the relative concentrations of yeast (YDM), sugar, and ethanol (EtOH) as a function of time when the yeast is propagated on a substrate of 1:1 date syrup (Dips)/molasses.

In order to eliminate Date syrup toxicity by dilution, substrates containing 2:1 and 1:1 Date syrup/molasses (w/w) were used for propagation. The performance of the yeast in the first 5 hours of propagation on both substrates was comparable to that on Date syrup and molasses (FIGS. 3 and 4 and Table 6). The overall biomass yields on sugar from the 2:1 substrate in this phase (calculated from FIGS. 3 and 4 and 104 g sugar fed) was 0.47, and that from the 1:1 substrate was 0.49 g/g, representing 94 and 98% of the theoretical values, respectively. In the rest of the propagation period the yields from the 2:1 substrate decreased more rapidly than those of the 1:1 substrate and reached 0.15 g/g in the last hour of propagation (Table 6). The biomass concentration at the end of propagation with the 2:1 substrate was about 28 g/l, 4.2 g/l ethanol was produced, and only traces of sugar remained unconsumed (FIG. 3). The overall average biomass yield on sugar was about 80% of the theoretical values, which was significantly higher than that from pure date syrup, but still significantly lower than that from molasses (Table 8). The concentration of formic acid in the fermentation broth at the end of propagation was 0.17-0.21 (Table 7). This concentration seemed to have reached the level of toxicity for the yeast production, and hence caused a decrease in the biomass yield. The biomass concentration at the end of propagation with the 1:1 substrate was about 31 g/l, 1.2 g/l ethanol produced, and only traces of sugar remained unconsumed (FIG. 4). The overall average biomass yield on sugar was about 93% of the theoretical value, and was not significantly different from that of molasses (Table 4). The concentration of formic acid in the fermentation broth at the end of propagation was 0.11-0.14 (Table 7). This concentration seemed to be tolerable to the yeast, and hence the biomass yield was not affected. In addition to the high yield obtained, the 1:1 date syrup/molasses substrate is superior to the other substrates, including molasses, in that it contains enough amounts of the essential vitamins m-Inositol and pantothenic acid that cover the needs of the yeast, and hence no addition to the medium is required.

Figure 5:
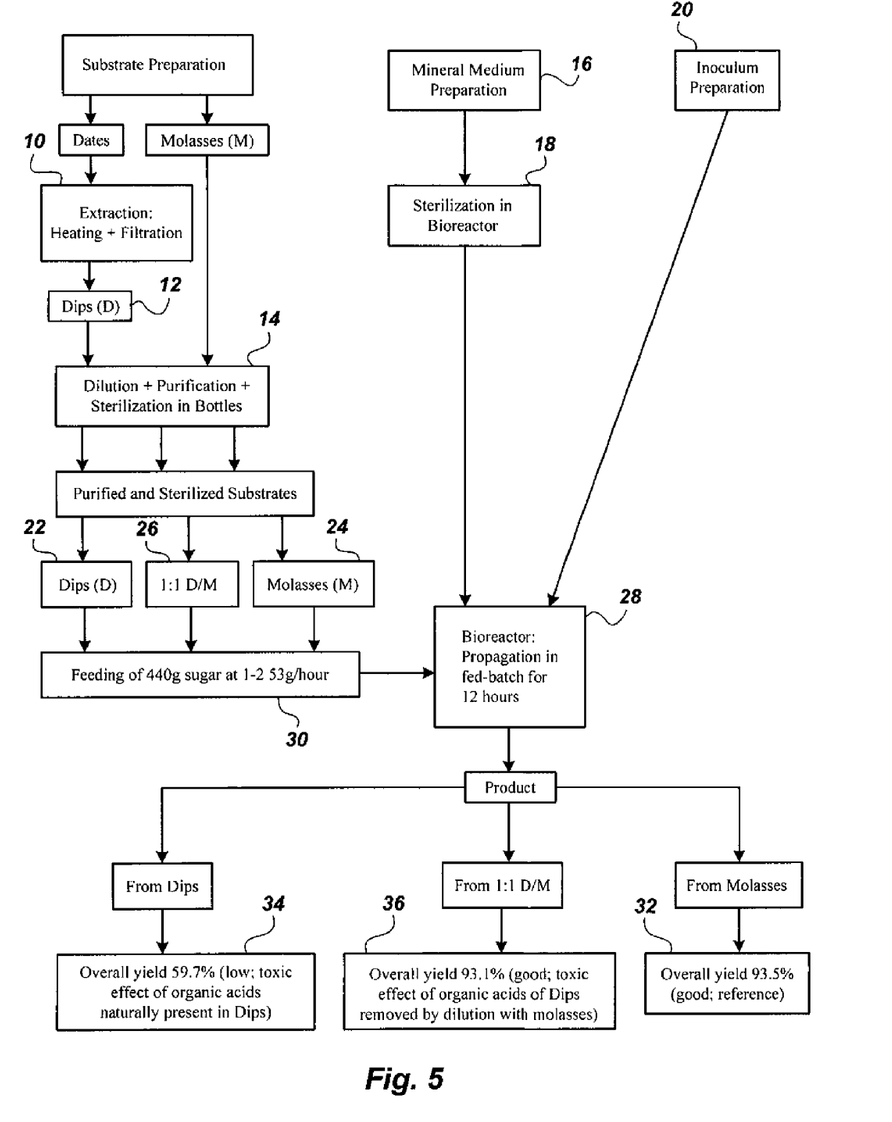
FIG. 5 is a flowchart schematically illustrating a method of producing baker's yeast according to the present invention.

FIG. 5 schematically summarizes the process and results achieved. The dates were processed by extraction using heating and filtration at step 10 to obtain the Dips syrup at 12. Both the Dips syrup and pure molasses were purified and sterilized (as described above) at step 14, and stored in bottles until required. The mineral medium was prepared at step 16 and sterilized in the bioreactor at step 18. The inoculum of S. cerevisiae was prepared as described above (step 20). The substrates (pure Dips 22, pure molasses 24, or a mixture of Dips/molasses 26) were placed in the bioreactor with the mineral medium and the inoculum and allowed to propagate for twelve hours (step 28), periodically adding additional substrate at a rate that gradually increased from 12 g/hr to 53 g/hr (step 30) in a fed-batch process, with periodic monitoring of sugar and alcohol levels. Molasses produced an overall yield of 93.5%, as indicated at 32, and served as a reference. Pure Dips only produced an overall yield of 59.7% (shown at 34), while the 1:1 mixture (w/w) of Dips and molasses produced a yield of 93.1% (shown at 36), which is comparable to pure molasses.

Although a 1:1 weight/weight mixture of Dips/molasses produced good results with the particular sample of date syrup derived from Rezez dates illustrated in Example 2, dilutions other than 1:1 (w/w) Dips/molasses may be required to produce good yields from date syrup extracted from other varieties of dates. It should be well within the ability of one of ordinary skill in the art to analyze the date syrup substrate to determine the presence and concentration of the toxins listed in Table 4 and to adjust the amount of molasses used to dilute the toxins in the date syrup to safe levels in order to produce an overall yield of Baker's yeast comparable to that obtained from pure molasses, thereby reducing the amount of molasses required and making use of a resource (dates) that would otherwise go to waste.

Example 3

Arabic bread has a round shape and forms pockets because of the high baking temperatures that make the dry exterior skin to set and carbon dioxide and water vapor to expand. These gasses disperse till the pressure is sufficient enough to force separation of the lower and upper layers, a phenomenon referred to as pocket formation. It has been reported that white flour produced from hard wheat with intermediate strength and protein content of 10-12% gave high quality Arabic bread. This example aims to evaluate the effect of using Baker's yeast produced using date syrup as a substrate on quality characteristics of Arabic bread.

The flour used in the experiments was commercial local flour from hard wheat (Yecora Rojo variety), extraction rate of 80% and production year 2006, obtained in 10-kg paper packs (Grain Silos and Flour Mills Organization, Dammam, Saudi Arabia). The flour had 13.4% protein and 0.65% ash.

For flour, the falling number was determined according to the method standardized by international bodies (Perten Instruments group, 2009), using the Perten instrument model 1700, Hagberg, Sweden. Flour (6.9 gram) was weighed based on 14% moisture content, transferred into the viscometer-tube tipped to 45 angle, 25 ml distilled water added, the tube shaken 10 times to obtain a uniform suspension of flour and water, and placed with a stirrer in the boiling water bath. The stirring apparatus was started immediately. Heating (about 100° C.), causes starch granules to swell and the viscosity of the suspension to increase. After stirring the sample for 60 seconds, the plunger was dropped for free fall. The rate and extent to which the viscosity of the starch suspension was reduced indicated the level of alpha amylase present. The optimum falling number is obtained in the reading between 200 and 300. This indicates optimal amylase activity, and due to this the wheat bread crumb is likely to be good.

Farinograph measures and records the resistance of dough to mixing. It is used to evaluate the water absorption capacity of the flour to determine the stability of dough during mixing. Measurement was done according to the AACC (1995) approved method 54-21 with the small (50 gram) mixing bowl of a Brabender farinograph (C.W. Brabender Instruments, Inc. South Hackensack, N.J., USA). After one minute dry mixing, sufficient water was added within 25 seconds, till maximum resistance was centered on the 500 Brabender Unit line. When the dough began to form, the sides of the bowl were scraped down with a plastic scraper, and the machine was permitted to run until an adequate curve was available (i.e. absorption, slightly beyond peak; stability, until top of curve recorded 500 BU line after peak; 12 minutes beyond the peak). The test was run three times, and then the absorption was calculated on a 14% moisture basis.

Gluten Indices of flour samples were determined by the AACC (1995) approved method 38-12 using the Glutomatic 2200 (Perten Instrument AB, Stockholm, Sweden). Wet gluten is washed from the flour sample, centrifuged through a sieve and the weight of wet gluten forced through the sieve and that of the total wet gluten were measured. The total wet gluten was expressed as percent of sample, and the gluten index was expressed as percentage of wet gluten remaining on the sieve after centrifuging.

Baking was made according to Qarooni et al., "A test baking technique for Arabic bread quality", J. Cereal Sci. 6: 69-80 (1987). A modified bread formula was chosen for this experiment. Dry ingredients: 700 g flour, 7 g salt, and 7 g yeast on dry weight basis (18 different bread treatments were prepared using the different produced baker's yeast treatments: molasses, date syrup, and 1:1 molasses to date syrup) at low and high flow rates, and were mixed at low speed for 1 min using Hobart mixer Model A-120 (The Hobart Manufacturing Company, Tory, Ohio), then water was added (30° C.) and mixing continued for 2 minutes at low speed, and then for 4 minutes at medium speed. The optimum amount of water was determined using the formula of Qarooni, "The Hand Book of Arabic Bread Production", published by Kuwait Flour Mills and Bakeries Co (S.A.K.) (1989) and Qarooni et al., "Production of Tanoor Bread with Hard White and Other U.S. Wheats", Lebensm.—Wiss. U.—Technol. 26: 100-106 (1993), with some modifications based on experimental experience (Baking absorption (%)=20+0.596 multiplied by the water absorption capacity determined by the farinograph test described above). The dough was then left to ferment in bulk for one hour at 30° C. and 85% relative humidity (rh), and then it was divided into pieces of 80 g, rounded by hand, covered with a cloth, and allowed to relax for 15 minutes in the same fermentation cabinet. These dough pieces were then flattened by hand and cross sheeted in a machine (0.8 mm thickness). All sheeted doughs were put in a wooden board and transferred into the proofing cabinet for 30 min at 30° C. and 85% rh. The proofed pieces were put on a pre-heated solid aluminum tray and baked at 425° C. for 100 seconds in a bench top furnace (Muffle-Thermolyne 6000 Series). Loaves were cooled for 15 min and wrapped in plastic bags.

Samples of dough prepared as described above were used for the estimation of yeast activity by measuring the gas production ability of the yeast. Measuring cylinders were used for assessing gas production ability. Twenty grams of dough was carefully placed in a 100-ml glass measuring cylinder, which was then incubated at 300° C. and 90% relative humidity in a National MFG incubator (National MFG. Co., Lincoln, Nebr.). The increase in dough volume due to $CO_2$ production was measured every 30 minutes for two hours.

The average protein content for flour (80% extraction) used in this study was 13.4%, which is somewhat higher than recommended, and may result in a decrease in dough strength and elasticity. It was also found that Farinograph water absorption was 66.6% for flour used in this study, which is within recommended ranges.

All reported data are average of three replicates. Gluten of tested flour indicated high wet gluten weight being 29.71 g. On the other hand, the gluten index value and dry gluten content were 99.36% and 11.85 g respectively.

The Falling Number is a method of determining the relative level of alpha amylase activity. The falling number of the experimental flour was 447 seconds. It has been reported that a falling number value of 350 seconds or longer indicate low enzyme activity and very sound wheat. As the amount of enzyme activity increases, the falling number decreases. Values below 200 seconds indicate high level of enzyme activity.

Samples of the prepared bread dough used for Arabic bread making were also used for estimation of yeast activity through gas production ability. Values of gas production power (ml/20 gm dough) of the experimental yeast are presented in (Table 9). It could be noted that there were significant differences due to the substrate used in yeast propagation, and also for the flow rate used. The highest significant effect on the gas production power was noticed for the flow rate. Usually the baker's yeast produced using the low flow rate showed significantly higher gas production power than those produced following the high flow rate system.

TABLE 9

Gas production power (ml/20 g dough) for baker's yeasts

| Run | Substrate | Flow Rate | Incubation Time (min.) | | | | |
|---|---|---|---|---|---|---|---|
| | | | Zero | 30 | 60 | 90 | 120 |
| Strain NCYC 1530 | | | | | | | |
| 13 | Molasses | Low | 18$^c$ | 31$^f$ | 42$^d$ | 44$^e$ | 45$^f$ |
| 14 | Molasses | High | 18$^c$ | 23$^l$ | 31$^h$ | 36$^j$ | 42$^i$ |
| 15 | Date Syrup | Low | 19$^b$ | 25$^j$ | 42$^d$ | 43$^f$ | 45$^f$ |
| 16 | Date Syrup | High | 18$^c$ | 34$^e$ | 43$^c$ | 44$^e$ | 46$^e$ |
| 17 | 1:1 | Low | 18$^c$ | 27$^h$ | 42$^d$ | 43$^f$ | 45$^f$ |
| 18 | 1:1 | High | 18$^c$ | 23$^l$ | 31$^h$ | 39$^h$ | 43$^h$ |
| | Control* | | 18$^c$ | 36$^c$ | 46$^a$ | 49$^a$ | 50$^a$ |

*Control = Hollandia Yeast.
$^{a-l}$ Within each column, means with the same letter are not significantly different.

Concerning the substrate used in the yeast production, it could be noticed there are insignificant differences for the gas production power between yeasts produced using either molasses or date syrup substrates. However the highest gas production power was noticed for yeasts produced using 1:1 molasses to date syrup substrate at the low flow rate system after 60, 90 and 120 minutes of incubation. These conditions of growth give biochemical properties of the yeast a special emphasis, and demand specific measures to ensure high quality and efficient dough aeration. The technological role of yeast in wheat flour dough is a strong alcoholic fermentation with extensive carbon dioxide liberation. The gassing power of pressed yeast depends on the zymase enzyme complex of the yeast cells, and available fermentable carbohydrates. The differences in the gassing power in the yeasts used in this work might be due to the various maltase and zymase activities of these yeasts.

The effect of the experimental baker's yeast strain produced from date syrup and molasses substrates under low and high flow rates on the quality of Arabic bread was investigated. Analysis of Variance (ANOVA) was performed to estimate the interaction effect among independent variables. Separation of means among all external and internal quality parameters were analyzed using least significant parameters, Fisher's (LSD) test.

The ANOVA analysis showing the effect of baker's yeasts from different fermentation treatments on Arabic bread quality can be observed in Table 10. There was strong interaction (Yeast*Substrate*Flow rate) effect on crust smoothness (p≦0.05) and shape (p≦0.01) values of Arabic bread. Breads made with yeasts from date syrup showed no significant decrease in crust smoothness and shape among all yeast strains compared to those produced using molasses. Arabic bread made with yeasts and produced under the following parameters: 1:1 molasses to date syrup, Hollandia yeast, and high flow rate (Treatment #12) showed the highest score for bread shape as compared with other treatments (Tables 11A-11D). All breads showed a marked significant variation in crust smoothness.

TABLE 10

F-Factors (Analysis of Variance) of Arabic Bread.

| Quality attribute | Yeast | Substrate | Flow rate | Yeast * Substrate | Yeast * Flow rate | Substrate * flow rate | Yeast * Substrate * Flow rate |
|---|---|---|---|---|---|---|---|
| Crust smoothness | 19.1*** | 7** | 51** | 4.8* | 16** | NS | 4.6** |
| Shape | 4.2* | 11.2** | NS | 8*** | 37.2*** | 7.5** | 99*** |
| Crust color | 6.3** | NS | NS | 14.75*** | 6.8** | NS | 6.2** |
| Cracks | 7.2** | 9.5** | 21.8** | 2.9* | 22.3*** | NS | 2.3*** |
| Blisters | 34*** | 8** | NS | 4.8* | 28.1*** | NS | 10.4*** |
| Roll & fold (1) | NS | 8** | 29.7** | NS | 7.5** | NS | 7*** |
| Separation of layers | NS | 13** | NS | 26*** | NS | 45*** | NS |
| Evenness of Layer | NS | NS | NS | 3.9** | NS | NS | 11.7*** |
| Grain appearance | NS | NS | NS | NS | NS | NS | NS |
| Grain uniformity | NS | NS | NS | NS | NS | NS | 3.3* |
| Crumb texture | NS | NS | NS | NS | NS | NS | NS |
| Tearing quality (1) | 5.4* | NS | 30.2** | NS | NS | NS | 3.6* |
| Crumb color | 18*** | 83.1*** | NS | NS | 7.1** | NS | NS |
| Roll & fold (2) | NS | 99*** | 402*** | 19.9*** | 25.*** | NS | 32*** |
| Tearing quality (2) | 133** | 18.6*** | NS | NS | 26.1*** | 24.5*** | 999*** |
| Total | 8** | 79*** | 29** | 8.5*** | 999*** | NS | 999*** |

*Significant at p ≦ 0.1
**Significant at p ≦ 0.05
***Significant at p ≦ 0.01
NS Not Significant Arabic bread showed a marked variation in crust color, cracks and blisters among all treatments. There is a strong significant interaction effect (Yeast*Substrate*Flow rate) on crust color (p≦0.05) as well as blister appearance and crakes (p≦0.01) of the Arabic bread, as shown in Table 10. It could also be noted from results of Tables 11A-11D that there were insignificant difference in crust color, cracks and blisters in case of using date syrup baker's yeast as compared with those of molasses, but yeast produced from 1:1 date syrup to molasses showed the highest score for these bread properties.

The ability of Arabic bread to roll and fold was evaluated for the first and second day after baking. There was a strong interaction effect (Yeast*Substrate*Flow rate) on the roll and fold features of Arabic bread in the first day and in the second day (P≦0.01) as can be seen from (Table 10). Arabic bread made with yeast produced using date syrup as a substrate, low flow rate and Hollandia yeast (treatment #9) scored the highest value on the ability to roll and fold on the first as well as on the second day (Tables 11A-11D).

There was insignificant interaction effect due to the (Yeast*Substrate*Flow rate) on the quality of separation of layers. However, there was a strong interaction effect (P≦0.01) due to the (Substrate*Flow rate) on the quality of separation of layers (Table 10). There was a significant interaction effect (P≦0.01) due to the (Yeast*Substrate*Flow rate) on the evenness of layers. Arabic breads showed insignificant variation in the scores of both separation and evenness of layers among all treatments (Tables 11A-11D), which indicates that use of date syrup baker's yeast resulted in good quality Arabic bread.

There was insignificant interaction effect due to the yeast, substrate, flow rate as well as their interactions on grain appearance, grain uniformity, crumb texture and crumb color. However, the only significant interaction effect (P≦0.01) was due to the (Yeast*Substrate*Flow rate) on the grain uniformity, and effect (P≦0.05) due to (Yeast*Flow rate) on crumb color. There was strong effect (P≦0.01) due to substrate on crumb color (Table 10). All Arabic breads showed no significant differences in values of grain appearance, grain uniformity and crumb texture among all treatments (Tables 11A-11D). Breads made with yeast produced from date syrup only showed the highest crumb color scores (Tables 11A-11D).

The ability of Arabic bread to tear in an acceptable manner was evaluated for the first and the second days. The interaction effect due to (Yeast*Substrate*Flow rate) on the tearing feature of Arabic white bread was significant in the first day and in the second day (P≦0.1) (Table 10). Tearing quality of Arabic bread made with NCYC 1530 Strain showed insignificant variations in tearing quality in the first day as could be seen from Tables 11A-11D. However, there was a marked significant variation in tearing quality of Arabic bread in the second day among all treatments (Table 10).

There was a significant interaction effect due to the (Yeast*Substrate*Flow rate) on the total score of the Arabic bread (P≦0.01), as can be seen in Table 10. Two treatments exhibited the highest overall total quality bread score. One of these two treatments was the Arabic breads made with yeast produced using date syrup, high flow rate, and NCYC 1530 yeast strain. The second was the Arabic bread with yeast made from 1:1 molasses to date syrup, NCYC 1530 yeast strain, and low flow rate. It has been reported that bread doughs prepared only from flour, water, yeast and salt (such as Arabic bread) will initially contain only about 0.5% of glucose and fructose derived from the flour. This is adequate to start fermentation and to activate the yeast's adaptive malto-zymase system that is responsible for maltose fermentation. Different yeast strains have been shown to vary in their maltase activity, and may also exhibit variable maltase activity under different dough conditions. Yeast itself brings same changes in the bread dough in the course of fermentation, such as depletion of fermentable substances; accumulation of products in the form of carbon dioxide, alcohols, acids and esters; modification of pH conditions; and softening or mellowing of the gluten character. In this present example, all of these factors may have contributed to the quality differences among baker's yeast produced in this study.

Baker's yeasts produced using the date syrup substrate gave baking results and gas production power comparable to those of yeasts produced from molasses, indicating that using date syrup as substrate for beaker's yeast production results in excellent quality yeasts to be used in baking industry.

TABLE 11A

Quality characteristic of Arabic bread from Saf-Instant Yeast

| Treatment | 1 | 2 | 3 | 4 | 5 | 6 |
|---|---|---|---|---|---|---|
| Substrate | Molasses | Molasses | Date Syrup | Date Syrup | 1:1 | 1:1 |
| Flow rate | Low | High | Low | High | Low | High |
| Crust smoothness (5) | $4.5^c$ | $4.7^c$ | $5^a$ | $4.8^{bc}$ | $5^a$ | $4.9^{ab}$ |
| Shape (8) | $6^d$ | $7^b$ | $7^b$ | $7^b$ | $7^b$ | $7^b$ |
| Crust color (8) | $7.8^{ab}$ | $7.7^{abc}$ | $8^a$ | $8^a$ | $8^a$ | $7.8^{ab}$ |
| Cracks (8) | $6.8^b$ | $6.9^{ab}$ | $6.9^{ab}$ | $6.9^{ab}$ | $6.9^{ab}$ | $6.9^{ab}$ |
| Blisters (8) | $8^b$ | $8^b$ | $8^b$ | $6.9^a$ | $6^b$ | $7.6^{cd}$ |
| Rolling and folding (1) (10) | $10^a$ | $10^a$ | $10^a$ | $10^a$ | $10^a$ | $10^a$ |
| Separation of layers (15) | $15^{ab}$ | $15^{ab}$ | $15^{ab}$ | $15^{ab}$ | $14.8^b$ | $15^{ab}$ |
| Evenness of layers (5) | $5^a$ | $5^a$ | $5^a$ | $5^a$ | $5^a$ | $5^a$ |
| Grain appearance (5) | $5^a$ | $5^a$ | $5^a$ | $5^a$ | $5^a$ | $5^a$ |
| Grain uniformity (5) | $5^a$ | $5^a$ | $5^a$ | $5^a$ | $5^a$ | $5^a$ |
| Crumb texture (8) | $7^a$ | $7^a$ | $7^a$ | $7^a$ | $7^a$ | $7^a$ |
| Tearing quality (1) (10) | $8^a$ | $8^a$ | $8^a$ | $8^a$ | $8^a$ | $8^a$ |
| Crumb color (5) | $4.8^{ab}$ | $4.6^c$ | $5^a$ | $5^a$ | $5^a$ | $4.8^{ab}$ |
| Rolling and folding (2) (30) | $13.3^{ef}$ | $11.3^{gh}$ | $13.9^{de}$ | $13.3^{ef}$ | $13.5^{de}$ | $9.3^c$ |
| Tearing quality (2) (20) | $9.3^c$ | $9.6^c$ | $9.8^{bc}$ | $9.6^c$ | $9.3^c$ | $9.5^c$ |
| Total (150) | $115.9^{hi}$ | $115.1^i$ | $119.8^{cde}$ | $116.5^{fgh}$ | $117.3^{efg}$ | $115.4^i$ |

TABLE 11B

Quality characteristic of Arabic bread from Hollandia Yeast

| Treatment | 7 | 8 | 9 | 10 | 11 | 12 |
|---|---|---|---|---|---|---|
| Substrate | Molasses | Molasses | Date Syrup | Date Syrup | 1:1 | 1:1 |
| Flow rate | Low | High | Low | High | Low | High |
| Crust smoothness (5) | $5^a$ | $4.5^c$ | $5^a$ | $5^a$ | $4.8^{bc}$ | $4.8^{bc}$ |

TABLE 11B-continued

Quality characteristic of Arabic bread from Hollandia Yeast

| Treatment | 7 | 8 | 9 | 10 | 11 | 12 |
|---|---|---|---|---|---|---|
| Shape (8) | $7^b$ | $6.7^b$ | $7^b$ | $7^b$ | $7^b$ | $7.9^a$ |
| Crust color (8) | $8^a$ | $7.8^{ab}$ | $7^e$ | $8^a$ | $7.7^{bc}$ | $7.9^{ab}$ |
| Cracks (8) | $6.9^{ab}$ | $6.9^{ab}$ | $6.9^{ab}$ | $6.9^{ab}$ | $6.9^{ab}$ | $6.9^{ab}$ |
| Blisters (8) | $7.8^{cb}$ | $8^b$ | $7.5^d$ | $8^b$ | $7.8^{bc}$ | $8.3^a$ |
| Rolling and folding (1) (10) | $10^a$ | $10^a$ | $10^a$ | $9.8^a$ | $10^a$ | $8.8^c$ |
| Separation of layers (15) | $15^{ab}$ | $15^{ab}$ | $15^{ab}$ | $15^{ab}$ | $15^{ab}$ | $15^{ab}$ |
| Evenness of layers (5) | $5^a$ | $5^a$ | $5^a$ | $5^a$ | $4.8^b$ | $5^a$ |
| Grain appearance (5) | $5^a$ | $5^a$ | $5^a$ | $5^a$ | $5^a$ | $5^a$ |
| Grain uniformity (5) | $5^a$ | $5^a$ | $5^a$ | $5^a$ | $5^a$ | $5^a$ |
| Crumb texture (8) | $7^a$ | $7^a$ | $7^a$ | $7^a$ | $7^a$ | $7^a$ |
| Tearing quality (1) (10) | $7.7^a$ | $8^a$ | $7.9^{ab}$ | $7.9^{ab}$ | $7.8^d$ | $7.9^c$ |
| Crumb color (5) | $4.5^d$ | $4.7^c$ | $5^a$ | $5^a$ | $4.8^{ab}$ | $5^a$ |
| Rolling and folding (2) (30) | $9.3^l$ | $9.3^l$ | $21.6^a$ | $14^{de}$ | $18^b$ | $12.3^{efg}$ |
| Tearing quality (2) (20) | $7^{de}$ | $6.2^a$ | $8^d$ | $9.6^c$ | $8^d$ | $9.3^c$ |
| Total (150) | $109.9^{jk}$ | $108.3^k$ | $123^a$ | $116.5^{cde}$ | $119^{bcd}$ | $116.1^{gh}$ |

TABLE 11C

Quality characteristic of Arabic bread from S. cerevisiae strain NCYC 1530 Yeast

| Treatment | 13 | 14 | 15 | 16 | 17 | 18 |
|---|---|---|---|---|---|---|
| Substrate | Molasses | Molasses | Date Syrup | Date Syrup | 1:1 | 1:1 |
| Flow rate | Low | High | Low | High | Low | High |
| Crust smoothness (5) | $5^a$ | $5^a$ | $5^a$ | $5^a$ | $5^a$ | $5^a$ |
| Shape (8) | $7^b$ | $6.6^{cb}$ | $7^b$ | $6.3^{cd}$ | $7^b$ | $6.1^d$ |
| Crust color (8) | $7.2^{de}$ | $7.5^{cd}$ | $8^a$ | $7.9^{ab}$ | $7.8^{ab}$ | $7.7^{bc}$ |
| Cracks (8) | $6.9^{ab}$ | $6.4^c$ | $6.9^{ab}$ | $6.9^{ab}$ | $7^a$ | $6.5^c$ |
| Blisters (8) | $8^b$ | $8^b$ | $8^b$ | $8^b$ | $8^b$ | $8^b$ |
| Rolling and folding (1) (10) | $9.8^a$ | $9.3^{bc}$ | $10^a$ | $9.6^{ab}$ | $9.6^{ab}$ | $9.6^{ab}$ |
| Separation of layers (15) | $15^{ab}$ | $14.6^c$ | $15^{ab}$ | $15^{ab}$ | $15^{ab}$ | $15^{ab}$ |
| Evenness of layers (5) | $5^a$ | $5^a$ | $5^a$ | $5^a$ | $5^a$ | $4.8^b$ |
| Grain appearance (5) | $5^a$ | $5^a$ | $5^a$ | $5^a$ | $5^a$ | $5^a$ |
| Grain uniformity (5) | $5^a$ | $5^a$ | $5^a$ | $5^a$ | $5^a$ | $5^a$ |
| Crumb texture (8) | $7^a$ | $7^a$ | $7^a$ | $7^a$ | $7^a$ | $7^a$ |
| Tearing quality (1) (10) | $8^a$ | $8^a$ | $8^a$ | $8^a$ | $8^a$ | $8^a$ |
| Crumb color (5) | $4.6^c$ | $4.5^d$ | $5^a$ | $5^a$ | $4.8^{ab}$ | $4.8^{ab}$ |
| Rolling and folding (2) (30) | $13.3^{ef}$ | $10^{hi}$ | $13.6^{de}$ | $16^c$ | $14^{de}$ | $15^c$ |
| Tearing quality (2) (20) | $12.3^a$ | $9^c$ | $12.3^a$ | $12^a$ | $12.6^a$ | $10.6^b$ |
| Total (150) | $116.1^{def}$ | $111^j$ | $120^{bcd}$ | $121^{ab}$ | $121^{ab}$ | $118.7^{cde}$ |

TABLE 11D

Quality characteristic of Arabic bread – Control = Hollandia Yeast

| Quality | Score |
|---|---|
| Crust smoothness (5) | $4.8^{bc}$ |
| Shape (8) | $6.9^b$ |
| Crust color (8) | $8^a$ |
| Cracks (8) | $7^a$ |
| Blisters (8) | $7.8^{bc}$ |
| Rolling and folding (1)(10) | $9.8^a$ |
| Separation of layers (15) | $15^{ab}$ |
| Evenness of layers (5) | $5^a$ |
| Grain appearance (5) | $5^a$ |
| Grain uniformity (5) | $5^a$ |
| Crumb texture (8) | $7^a$ |
| Tearing quality (1)(10) | $7.8^{ab}$ |
| Crumb color (5) | $5^a$ |
| Rolling and folding (2)(30) | $13^f$ |
| Tearing quality (2)(20) | $9^c$ |
| Total (150) | $115.1^i$ |

In Tables 11A through 11D, the same letter superscript means not significantly different It is to be understood that the present invention is not limited to the embodiments described above, but encompasses any and all embodiments within the scope of the following claims.

We claim:

1. A method of producing baker's yeast, comprising the steps of:
   preparing a substrate containing a 1:1 mixture (w/w) of date syrup and molasses, wherein the date syrup is extracted from Rezez dates and the molasses is produced from sugar cane;
   inoculating the substrate with Saccharomyces cerevisiae yeast;
   placing the inoculated substrate in a fermentation vessel;
   propagating the yeast under fermentation conditions, wherein propagation was a fed-batch process, at 30° C., 8 g/l inoculum size, 6.0 liter starting volume, and sugar concentration in the substrate was 200 g/l;

periodically feeding additional substrate to the propagating yeast in quantities calculated to maintain yeast growth at a rate that avoids respirofermentative growth and formation of ethanol; and collecting viable yeast when propagation ceases.

2. The method of producing of baker's yeast according to claim 1, further comprising the step of adding an effective amount of ammonium sulfate and ammonium phosphate to the substrate in order to supply quantities of nitrogen, phosphorus, and sulfur lacking in the substrate but required for propagation of the yeast.

3. The method of producing of baker's yeast according to claim 1, further comprising the step of adding sulfuric acid to the substrate to adjust the pH to about 4.5.

4. The method of producing of baker's yeast according to claim 1, further comprising the step of stirring the inoculated substrate in the fermentation vessel to aerate the mixture.

5. Arabic bread leavened with yeast produced according to the method of claim 1.

6. A method of producing of baker's yeast, comprising the steps of:
   analyzing date syrup to determine concentrations of organic acids toxic to yeast present in the date syrup;
   diluting the date syrup with a volume of molasses sufficient to lower the concentrations of the toxic organic acids to safe levels, thereby forming a substrate, wherein the substrate is a 1:1 mixture (w/w) of date syrup and molasses, wherein the date syrup is extracted from Rezez dates and the molasses is produced from sugar cane;
   inoculating the substrate with Saccharomyces cerevisiae yeast;
   placing the inoculated substrate in a fermentation vessel;
   propagating the yeast under fermentation conditions, wherein propagation was a fed-batch process, at 30° C., 8 g/l inoculum size, 6.0 liter starting volume, and sugar concentration in the substrate was 200 g/l;
   periodically feeding additional substrate to the propagating yeast in quantities calculated to maintain yeast growth at a rate that avoids respirofermentative growth and formation of ethanol; and
   collecting viable yeast when propagation ceases.

7. The method of producing of baker's yeast according to claim 6, further comprising the step of adding an effective amount of ammonium sulfate and ammonium phosphate to the substrate in order to supply quantities of nitrogen, phosphorus, and sulfur lacking in the substrate but required for propagation of the yeast.

8. The method of producing of baker's yeast according to claim 6, further comprising the step of adding sulfuric acid to the substrate to adjust the pH to about 4.5.

9. The method of producing of baker's yeast according to claim 6, further comprising the step of stirring the inoculated substrate in the fermentation vessel to aerate the mixture.

10. Arabic bread leavened with yeast produced according to the method of claim 6.

11. The method of producing of baker's yeast according to claim 6, wherein the organic acids toxic to yeast present in the date syrup are selected from the group consisting of formic acid, acetic acid, and propionic acid.

12. The method of producing of baker's yeast according to claim 6, wherein the step of diluting the date syrup comprises diluting the date syrup with a volume of molasses sufficient to lower the concentration of any formic acid in the date syrup to less than 0.25% (w/v).

13. The method of producing of baker's yeast according to claim 6, wherein the step of diluting the date syrup comprises diluting the date syrup with a volume of molasses sufficient to lower the concentration of any acetic acid and propionic acid, added together, in the date syrup to less than 3% (w/v).

* * * * *